United States Patent [19]

Cosyns et al.

[11] 4,191,632
[45] Mar. 4, 1980

[54] PROCESS FOR THE PRODUCTION OF BENZENE FROM HYDROCARBON FRACTIONS RICH IN ALKYL-AROMATIC HYDROCARBONS AND CONTAINING PARAFFINIC AND NAPHTHENIC HYDROCARBONS

[75] Inventors: Jean Cosyns, Maule; Christian Marcilly, Houilles; Jean Miquel, Paris; Jean-Francois Le Page, Rueil Malmaison, all of France

[73] Assignee: Institut Francais du Petrole, Rueil-Malmaison, France

[21] Appl. No.: 893,912

[22] Filed: Apr. 6, 1978

[30] Foreign Application Priority Data

Apr. 6, 1977 [FR] France .................. 77 10685

[51] Int. Cl.² .................. C07C 3/58; C10G 37/10
[52] U.S. Cl. .................. 585/483; 208/59; 252/455 Z; 585/489; 585/841; 208/57
[58] Field of Search .............. 208/57, 59; 260/672 R, 260/672 NC

[56] References Cited

U.S. PATENT DOCUMENTS

| 3,267,023 | 8/1966 | Miale et al. ................ 260/672 R |
| 3,296,323 | 1/1967 | Myers et al. ................ 260/672 R |
| 3,310,593 | 3/1967 | Nelson et al. ............... 260/672 R |
| 3,775,298 | 11/1973 | Morris et al. ................ 208/59 |
| 4,150,061 | 4/1979 | Feinstein et al. ............ 260/672 R |

Primary Examiner—Herbert Levine
Attorney, Agent, or Firm—Millen & White

[57] ABSTRACT

A process for producing benzene is provided which comprises the steps of subjecting a charge rich in alkyl-aromatic hydrocarbons and containing 2–20% by weight paraffinic and/or naphthenic hydrocarbons, in a first catalytic zone, to a hydrotreatment in the presence of a catalyst mixture containing a selective mordenite catalyst and a reforming catalyst, then subjecting at least a portion of the resultant effluent to thermal or catalytic hydrodealkylation in a second zone, and separating and recovering benzene from the effluent from the second zone.

10 Claims, 1 Drawing Figure

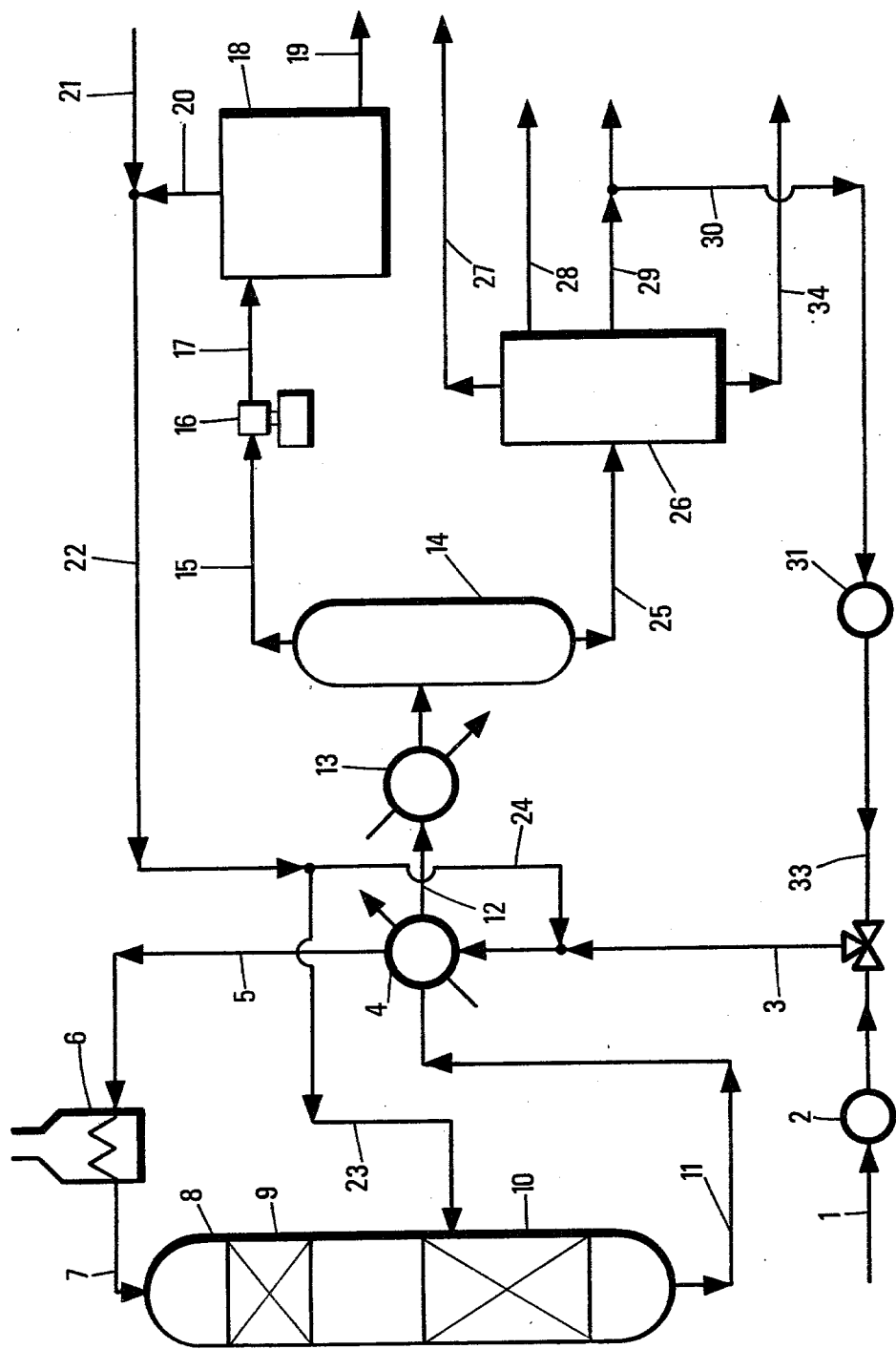

PROCESS FOR THE PRODUCTION OF BENZENE FROM HYDROCARBON FRACTIONS RICH IN ALKYL-AROMATIC HYDROCARBONS AND CONTAINING PARAFFINIC AND NAPHTHENIC HYDROCARBONS

BACKGROUND OF THE INVENTION

The production of benzene by hydrodealkylation of toluene or of hydrocarbons of the polysubstituted methyl-aromatic type has been practiced for many years. The operation takes place under hydrogen pressure at temperatures of between 530° and 720° C.; the reaction may be activated either by heat alone or by heat and a catalyst. When activation is thermal, the operation takes place between 620° and 720° C., and when activation is catalytic, temperatures of between 530° and 650° C. are preferably used, depending upon the activity of the catalyst employed. When the charge to be treated consists mainly of aromatic hydrocarbons as are the charges emanating from an extraction unit or a high-duty reforming plant, the operation is found to be a quite straightforward one, but it becomes complicated when the charge to be treated contains a certain proportion of saturated hydrocarbons of the naphthenic or paraffinic type (normal or iso paraffinic hydrocarbons), such as the charges emanating from a low-duty reforming plant or from a steam-cracking installation or a unit for the distillation of the light condensates of coke-ovens. In this last-mentioned case, the presence of paraffinic and naphthenic products, the content of which may vary from 2 to 20% by weight, increases the exothermicity of the operation, since the saturated products are converted mainly into methane, and furthermore, there will also be a tendency to accelerate the deposition of coke in the reaction vessel and especially when the reaction vessel is filled with catalyst; therefore, in the art as hitherto practised, it has been preferred to use thermal activation without using a catalyst even if the operation has to be carried out at a higher temperature with all the inconveniences that can be caused by the use of elevated temperatures as regards the nature of the materials used for the construction of the ovens or the reaction vessel.

DETAILED DISCUSSION

The object of the present invention is to permit the best possible use, during hydrodealkylation of the charge, of the heat resulting from the hydrogenolysis of the paraffins and naphthenes contained in this charge, so as to bring the charge to the temperature required for hydrodealkylation of the alkyl-aromatics and especially of toluene. In this process, the charge contains at least 60% by weight of alkyl-aromatic hydrocarbons as well as 2 to 20% approximately by weight of hydrocarbons selected from the naphthenic, paraffinic and iso-paraffinic hydrocarbons or mixtures thereof, this charge preferably containing alkyl-aromatic hydrocarbons containing 7 to 9 atoms of carbon per molecule, this charge being for example a toluene-xylene cut emanating from a reforming installation or a steam-cracking plant; (in the case where the charge is obtained from a steam-cracking plant, it will be hydro-treated beforehand in the conventional manner so as to eliminate selectively olefinic, diolefinic, sulphurized, nitrogenized and other compounds likely to interfere with the performance of the process). In the method in accordance with the invention, the charge, after having been preheated in an oven, is treated with hydrogen on a first catalyst bed where the hydrocracking and hydrogenolysis of the paraffin and iso-paraffins are carried out selectively without the aromatics (and the naphthenes if contained in the charge) being able to react. The catalyst used in this first catalytic bed or zone is mordenite which contains less than 0.6% of sodium by weight, for example 0.2 to 0.6% by weight, and which contains at least one metal of the VIII and IB groups, which metal is selected in particular from nickel, cobalt, copper and silver. The mordenite preferably contains 1 to 2.5% of nickel and/or 1 to 2.5% of cobalt and/or 2 to 3% of copper and/or 5 to 18% of silver. Such a mordenite is obtained in the following manner. The starting material is a soda mordenite containing approximately 5 to 8% of sodium by weight and having a pore size of between approximately 5 and 6 Å. This soda mordenite is exchanged with compensation cations selected from the cations of the metals of groups VIII and IB of the Periodic Table, and particularly from the cations of at least one of the following metals: nickel, cobalt, copper and silver. After exchange, the pore size is maintained at approximately 5-6 Å so that only the paraffins and iso-paraffins are able to reach the internal pores of the zeolite where hydrocracking and hydrogenolysis take place. Since the dimensions of the naphthenic and aromatic molecules are too great to enable them to reach the interior of these same pores, they pass through this first catalytic bed without being converted. The required metal or metals (Ni, Co, Cu, Ag) may be introduced, not by the exchange mentioned above, but in the form of an acetate or other salt (for example an ammoniacal complex) introduced into a soda mordenite, the sodium content of which is previously reduced by an acid treatment (hydrochloric acid for example) carried out to reflux during a period of some twenty hours, or so.

The first catalytic zone operates under a pressure of 10 to 50 bars, preferably 20 to 30 bars, at a spatial velocity of between 0.1 and 10 and preferably between 0.5 and 5 cm$^3$ of liquid charge per cm$^3$ of catalyst and per hour, with a H$_2$/hydrocarbon ratio of between 2 and 10, expressed in moles, and preferably between 4 and 6, and at a temperature of between 450° and 570° C., and preferably 500°–570° C. The temperature on entry into the first catalytic bed is preferably so adjusted that the heat from the reaction of the paraffinic compounds with the hydrogen used is able to raise the temperature of the reaction mixture at least partway to the level required for carrying out the hydrodealkylation reaction itself, this reaction being carried out thermally at between 620° and 720° C., or catalytically at between 500° and 650° C. however, the preliminary hydrocracking will be best exploited by using the catalytic form of hydrodealkylation at the lowest possible temperature, preferably between 500° and 570° C., in the presence of a catalyst different from that of the first catalytic bed. The catalyst of the second bed is not mordenite.

The other operating conditions used in the catalytic hydrodealkylation zone are as follows: the pressure is between 10 and 50 bars and preferably between 20 and 30 bars, the spatial velocity is between 0.1 and 10, say, between 1 and 6, and preferably between 2 and 4, and the H$_2$/hydrocarbon molar ratio is between 2 and 10 and preferably between 4 and 6.

When a catalyst is used for hydrodealkylation, the catalysts are those described in particular in French Pat.

Nos. 2 254 542, 74 07340, 2 268 772 and 74 30692 and French Pat. of Addition No. 75 02678. Use is preferably made of the catalysts of French Pat. Nos. 74 07240 and 75 02678, that is to say a catalyst which mainly contains:
   (a) a carrier capable of absorbing simultaneously all of the paraffinic, iso-paraffinic, naphthenic and aromatic hydrocarbons, that is to say a carrier having no selectivity. This carrier is selected from the aluminas, silicas, silica-aluminas, magnesias, silica-magnesias, acid aluminas, chlorine-containing or fluorine-containing alumina, boron aluminas, zirconias, metallic aluminates or mixtures of these various compounds.
   (b) at least one metal selected from nickel, ruthenium, osmium, palladium, rhodium, iridium and platinum, the metal content being between 0.05 and 5% by weight of the catalyst, or the metal selected may be cobalt, the cobalt content varying from 0.05 to 20% by weight, and optionally,
   (c) at least one metal selected from zinc, cadmium, gallium, indium, thallium and germanium, the content of metal or metals selected being between 0.05 and 5% by weight of catalyst.

A simplified layout illustrating the process as described is shown in FIG. 1.

A mixture of fresh charge, arriving through a pipe 1 and a pump 2, and of a recycled toluene fraction, arriving through a pump 31 and a pipe 33, passes through a pipe 3 into which is also fed hydrogen introduced through a pipe 24. The mixture is heated by the effluent from a reaction vessel 8 by being passed into an exchanger system 4, and the mixture is then passed into a stove 6 through a pipe 5, and through a line 7 it is introduced into the hydrotreatment reaction vessel 8 where it encounters a first catalytic bed 9, consisting mainly of small-pore mordenite, where the temperature of the reaction mixture rises due to the exothermicity resulting from cracking of the paraffins contained in the charge. At the outlet of the catalytic bed 9, the reaction mixture passes to a hydrodealkylation bed 10; the two beds, arranged in series, ar here superposed by they could be arranged side-by-side, a suitable means being provided to pass the catalyst from one bed to the other. In the bed 10, the alkyl-aromatic hydrocarbons are converted in amounts varying between 60 and 90%. The effluent from the bed 10 is extracted through a pipe 11 and passes through the exchanger system 4. Through a pipe 12 the effluent is passed to an exchanger 13 where it is partially condensed, and reaches a separator 14 which separates a methane-rich gaseous phase, which is extracted through pipe 15, and a mainly aromatic liquid phase which is extracted through a pipe 25. The liquid phase passes to a distillation system 26 where the following are extracted:
   a very small fraction of paraffinic hydrocarbons containing 2 to 5 atoms of carbon per molecule—extracted through pipe 27,
   a benzene fraction constituting a usable product—extracted through pipe 28,
   a fraction containing toluene as well as aromatic hydrocarbons of the unconverted charge, part at least of this fraction being recycled through a pipe 30 to the pump 31 and from there to the reaction vessel 8; this fraction is extracted through pipe 29,
   a heavy aromatic fraction which is preferably not recycled to the hydrotreatment reactor; this fraction is extracted through pipe 34.

The gaseous fraction leaving the separator 14 through the pipe 15 is recompressed at 16 and passed through a pipe 17 into the purifying unit 18 to enrich the gaseous fraction with hydrogen and to separate it from the hydrocarbons, mainly methane and ethane, which are produced during the reaction. This purification can be carried out in equipment of the demethanizing type which operates at very low temperature or by absorption on molecular sieves, the object being in both cases to obtain, in the gas from the pipe 20, a molar hydrogen content greater than 90%. The purified gas from the pipe 20 is then mixed with fresh hydrogen gas introduced through a pipe 21; it is also possible to form this mixture before purification if the molar hydrogen content in the added gas is less than 90% as is the case when the added gas is a hydrogen gas obtained from a catalytic reforming installation or from a steam-cracking plant. At least part of the mixture of recycling gas and added gas is passed, through pipes 22 and 24, into the line 3 for introduction into the reaction vessel 8. Optionally, a part of this gas mixture can be diverted and injected through pipe 23 into one or more areas of the hydrodealkylation bed 10 so as to avoid excessive increase in the temperature in the body of this catalytic bed.

In the case where the charge to be treated contains considerable quantities of naphthene (more than 3% by weight for example) and particularly when this charge is a fuel which comes from a steam-cracking operation and which may contain more than a very small amount of naphthenes, and advantageous variant of this arrangement comprising catalytic beds arranged in series consists in using in the first bed, not one single catalyst of the mordenite type having geometric selectivity, but a mixture of this catalyst with a mono- or multi-metal reforming catalyst; in these conditions, the paraffins are still eliminated, but the major portion of the naphthenes contained in the charge are converted into aromatic hydrocarbons. This correspondingly increases the aromatic hydrocarbon yield and still increases the benzene yield on completion of hydrodealkylation. In this variant in which two conversions, one exothermic and the other exothermic, take place, the calorific balance is such that the increase in temperature along the catalytic bed is small, and it is necessary to increase, to approximately 500° C., the temperature at which the reaction medium enters the reaction vessel. The proportion of reforming catalyst represents approximately 30 to 70% by weight of the mordenite-base catalyst, and preferably 40 to 60%.

EXAMPLE 1

The charge to be treated was a toluene-rich cut from a direct-distillation reforming treatment, and its composition is shown in Table I. Treatment took place on two catalytic beds arranged in series and operating under the conditions indicated in Table II.

TABLE I

| Composition of charge (% by wt.) | | | |
|---|---|---|---|
| number of carbon atoms | aromatics | naphthenes | normal and iso-paraffins |
| 6 | 3.5 | ≦0.05 | 0.4 |
| 7 | 79.4 | 0.2 | 5.4 |
| 8 | 6.1 | ≦0.05 | 4.9 |
| 9+ | — | — | 0.1 |

TABLE II

| 1st bed (hydrogenolysis) | 2nd bed (hydrodealkylation) |
|---|---|
| catalyst: mordenite, small pores, exchanged with nickel. (2.5% by wt.) of nickel. | catalyst: CO+ Zn+ Ni on nickel aluminate and alumina |
| P: 20 bars | P: 20 bars |
| $H_2$/HC molar ratio: 5 | $H_2$ + $CH_4$/HC molar ratio: 5 |
| T: 490° C. | T: 535° C. |
| Spatial velocity (cm³ of liquid charge per cm³ of catalyst and per hour): 2 | Spatial velocity: 2 |

The catalyst of the first bed was a small-pore mordenite (5.5 Å) in the form of extrusions. It was prepared from a soda mordenite, marketed by CECA, by triple exchange of the sodium ions for ammonium ions provided by $NO_3NH_4$; each exchange consisted in passing 8 volumes of an aqueous ammonium nitrate solution (1.66 mol of ammonium nitrate per liter) by weight of initial mordenite, at a pH value of 9 and an ambient temperature (duration 6 hours). Each exchange was followed by washing. After the third exchange the mordenite contained 0.25% by weight of sodium. A fourth exchange in the presence of $Ni(NO_3)_2$ enabled the ammonium ions to be exchanged for nickel ions. This exchange was carried out by passing 6.7 volumes of a nickel nitrate solution (concentration: 1.5 mole of nickel nitrate per liter) by weight of dry mordenite (obtained after the third exchange), at a pH value of 5.6 and at ambient temperature. The catalyst was then dried for 4 hours at 100° C. and at atmospheric pressure in air, after which it was then calcinated for 3 hours at 500° C. The catalyst was reduced in a stream of hydrogen for 2 hours in the reaction vessel itself. The catalyst contained, by weight, 0.25% of sodium and 2.5% of nickel.

The catalyst of the second bed was a hydrodealkylation catalyst based on cobalt oxide (15% by weight of cobalt) and zinc oxide (1% by weight of zinc) deposited on nickel aluminate and alumina. The nickel aluminate was itself prepared by depositing nickel nitrate on a transition alumina having a specific area of 200 m²/g, and this deposition was followed by calcination in air at 850° C. for 4 hours so as to convert the nickel nitrate into nickel aluminate. After deposition of the cobalt and zinc on the nickel aluminate by moistening the aluminate carrier in an aqueous solution of cobalt nitrate and zinc nitrate, the catalyst was calcinated at 550° C. in air for 3 hours and was then reduced in the reaction unit at 580° C. in a stream of hydrogen. The catalyst contained in all 15% by weight of cobalt, 1% by weight of zinc, 10% by weight of nickel, 30% by weight of alumina in the form of nickel aluminate, and 60% by weight of alumina.

The experiment was carried out in a gradient reaction vessel containing two 50 cm³ catalyst beds, each of which operated under the conditions indicated by Table II, the liquid charge being fed into the reaction vessel at a rate of 100 cm³ per hour.

The results obtained are shown in Table III. Column 2 shows the performances obtained after 24 hours experimentation and column 3, after 240 hours. The molar benzene yield corresponds to the number of benzene molecules obtained in relation to the number of alkylbenzene molecules that had reacted.

TABLE III

| Products | Weight of products obtained for each 1000 g of injected liquid charge | |
|---|---|---|
| | 24th hour | 240th hour |
| Benzene | 457 | 445 |
| Toluene | 320 | 336 |
| Xylenes | 13 | 14 |
| Total naphthenes | 0.05 | 0.05 |
| Total paraffins 5+ carbon atoms | — | — |
| Molar benzene yield | 96.5 | 97 |

EXAMPLE 2

Hydrogenolysis was carried out at 510° C. and hydrodealkylation at 550° C., the other operating conditions as well as the catalysts and the composition of the charge being the same as those of Example 1. Conversion of toluene into benzene was noticeably increased without significant deactivation of the catalyst, as shown by the results given in Table IV.

TABLE IV

| Products | Weight of products obtained for each 1000 g of injected liquid charge | |
|---|---|---|
| | 24th hour | 240th hour |
| Benzene | 565 | 550 |
| Toluene | 190 | 207 |
| Xylenes | 9 | 11 |
| Total naphthenes | ~0.02 | ~0.02 |
| Total paraffins 5+ carbon atoms | — | — |
| Molar benzene yield | 96.3 | 96.2 |

EXAMPLE 3

A test was carried out by directly attacking the second hydrodealkylation bed at 550° C. as in Example 2, but without treating the charge on a first catalyst bed for the hydrogenolysis and the hydro-cracking of the paraffins, the other operating conditions being the same as those used in Example 2 in the second bed. The results, contained in Table V, shown that the initial conversion of the toluene was substantially the same as in Example 2, but a distinct deactivation of the catalyst was observed at the end of 240 hours operation. Thus, preliminary hydro-decomposition of the heavy paraffins to form very light paraffins greatly increases the stability of the hydrodealkylation operation.

TABLE V

| Products | Weight of products obtained for each 1000 g of injected liquid charge | |
|---|---|---|
| | 24th hour | 240th hour |
| Benzene | 548 | 375 |
| Toluene | 208 | 407 |
| Xylenes | 11 | 26 |
| Total naphthenes | ~0.02 | 0.05 |
| Total paraffins 5+ carbon atoms | 0.7 | 2.8 |
| Molar benzene yield | 95.8 | 96.3 |

EXAMPLE 4

The charge to be treated was an aromatic cut (90°–150° C.) resulting from a steam-cracking operation in which the diolefins, olefins and alkenyl-aromatic hydrocarbons had been previously converted into paraffins and alkyl-aromatic hydrocarbons and wherein sulphur had been eliminated by hydro-treatment. The composition by weight of the charge is shown in Table IV (columns 1 and 2). The operating conditions and the catalysts used were the same as those indicated in Table II (Example 1). On completion of the operation, the paraffins and naphthenes having more than 6 carbon atoms had been converted. The weights of the various aromatic hydrocarbons collected at the outlet of the unit for each 1000 grams of injected liquid charge are shown in columns 3 and 4 of Table VI. Column 3 shows the balance obtained between the 48th and 60th hours, and column 4 the balance obtained between the 228th and 240th hours. The molar benzene yield was 102 on new catalyst, showing that a portion of the naphthenes were in the form of benzene, but this yield tended to diminish with ageing of the catalyst. This ageing is due to the presence of naphthenes on the hydrodealkylation catalyst, which naphthenes were unable to gain access to the catalyst of the first bed for reasons of steric space requirements. Consequently a slight reduction in conversion and selectivity occurred in the course of time.

TABLE VI

| Composition by wt. of the charge for each 1000 g of liquid charge | | Weight of aromatic products obtained for each 1000 g of injected charge | |
|---|---|---|---|
| | | 48–60th hour | 228–240th hour |
| Benzene | 43.4 | 526.0 | 492.5 |
| Toluene | 609.0 | 183.0 | 212 |
| Ethylbenzene | 95.0 | 9.5 | 14 |
| Xylenes | 76.0 | 12 | 18 |
| Aromatics with 9 C atoms | 2.0 | 0.5 | 0.6 |
| Methylcyclopentane | 1.0 | — | — |
| Cyclohexane | 2.1 | 0.3 | 0.4 |
| Naphthenes with 7 C atoms | 81.0 | — | — |
| Naphthenes with 8 C atoms | 25.0 | — | — |
| Naphthenes with 9 and 10 C atoms | 4.5 | — | — |
| Paraffins with 7 C atoms | 22.7 | — | — |
| Paraffins with 8 C atoms | 26.3 | — | — |
| Paraffins with 9 and 10 C atoms | 12.0 | — | — |
| Molar benzene yield: + Δ benzene product − Δ converted alkyl-aromatics | | 102 | 100 |

EXAMPLE 5

The composition of the charge is given in Table VIII. The first catalyst bed was a mixture comprising 50% by weight of a reforming catalyst containing 0.6% of platinum, 0.05% of iridium and 1.2% of chlorine deposited on a γ-alumina having a specific area of 250 m²/g in the form of extrusions, and 50% by weight of the previously used mordenite-base catalyst. The second catalyst bed was the same as those mentioned in the previous Examples. The operating conditions used are shown in Table VII.

TABLE VII

| | 1st bed | 2nd bed |
|---|---|---|
| Catalyst | Mixture of small-pore mordenite exchanged with nickel (50%) and reforming catalyst (50%) | Co (15% by wt.) + Zn (1% by wt.) on nickel aluminate |
| Pressure | 20 bars | 20 bars |
| T in °C. | 520 | 510 |
| Spatial velocity | 1 (in cm³ of liquid charge per cm³ of catalyst and per hour) | 2 |
| H₂/HC molar ratio | 5 | 5 |

The results obtained after three different operating periods are shown in Table VIII. The benzene yield in relation to the alkyl-aromatics contained in the charge was slightly increased and remained almost constant with time; elimination of naphthenes before the reaction medium reached the hydrodealkylation catalyst bed greatly increased the stability of the operation both as regards conversion and selectivity, taking into account the fact that the reforming catalyst permitted conversion of a considerable proportion of the naphthenes into corresponding aromatic hydrocarbons.

TABLE VIII

| Composition by wt. of the charge for each 1000 g of liquid charge | | Weight of aromatic products obtained for each 1000 g of injected charge | | |
|---|---|---|---|---|
| | | 48–60th hour | 228–240th hour | 600–612th hour |
| Benzene | 43.4 | 525.4 | 520 | 518.6 |
| Toluene | 609.0 | 191 | 198 | 196 |
| Ethylbenzene | 95.0 | 8.2 | 7.5 | 8.3 |
| Xylenes | 76.0 | 11 | 12 | 11.5 |
| Aromatics with 9 C atoms | 2.0 | 0.6 | 0.5 | 0.5 |
| Methylcyclopentane | 1.0 | — | — | — |
| Cyclohexane | 2.1 | 0.1 | 0.1 | 0.1 |
| Naphthenes with 7 C atoms | 31.0 | — | — | — |
| Naphthenes with 8 C atoms | 25.0 | — | — | — |
| Naphthenes with 9 and 10 C atoms | 4.5 | — | — | — |
| Total-paraffins with 7, 8, 9 and 10 C atoms | 61 | — | — | — |
| Molar benzene yield | — | 103.2 | 103.4 | 102.8 |

We claim:

1. A process for the production of benzene which comprises the steps of:
    subjecting a hydrocarbon charge, rich in alkyl-aromatic hydrocarbons and containing approximately 2 to 20% by weight of iso and normal paraffinic hydrocarbons and naphthenic hydrocarbons or mixtures of these hydrocarbons, in a first catalytic zone, to a hydro-treatment carried out at a temperature of between 450° and 570° C. under a pressure of between 10 and 50 bars at a spatial velocity of between 0.1 and 10 cm³ of liquid charge per cm³ of catalyst and per hour with a H₂/hydrocarbon molar ratio of between 2 and 10, in the presence of a catalyst, said catalyst being a mixture containing (a) a mordenite containing less than 0.6% by weight of sodium, and having a pore size of between approximately 5 and 6 Å and containing cations selected from the cations of the metals of groups VIII and IB of the Periodic Table, and (b) a reforming catalyst, the proportion of the latter forming 30 to 70% by weight of the mordenite;
    passing at least a portion of the effluent from said first catalytic zone into a second zone and subjecting said effluent to hydrodealkylation, carried out either thermally at a temperature of between 620° and 720° C. or catalytically on a second catalytic bed at a temperature of between 500° and 650° C. under a pressure of between 10 and 50 bars, at a liquid spatial velocity of between 0.1 and 10, with a H₂/hydrocarbon molar ratio of between 2 and 10, the catalyst of said second catalytic bed comprising a non-selective carrier; and
    separating and recovering benzene from the effluent from said second zone.

2. A process according to claim 1, wherein the non-selective carrier is selected from the aluminas, silicas, silica-aluminas, magnesias, silica-magnesias, acid aluminas, chlorinated or fluorinated aluminas, boron-aluminas, zirconias, silica-zirconias, metallic aluminates or mixtures of these compounds.

3. A process according to claim 1, wherein the charge emanates from a reforming installation or a steam-cracking plant and contains aromatic hydrocarbons having mainly 7 to 9 atoms of carbon per molecule.

4. A process according to claim 3, wherein the charge emanates from a steam-cracking plant, and wherein said charge is first subjected to a hydrotreatment to eliminate the olefinic and sulphurized compounds.

5. A process according to claim 3, wherein the first catalytic zone operates at a temperature of between 520° and 570° C. and under a pressure of between 20 and 30 bars, at a spatial velocity of between 0.5 and 5 $cm^3$ of liquid charge per $cm^3$ of catalyst and per hour, with a $H_2$/hydrocarbon molar ratio of between 4 and 6.

6. A process according to claim 5, wherein the mordenite of the first catalytic zone has a pore size of between 5 and 6 Å after exchange with compensation cations selected from the cations of at least one metal selected from nickel, cobalt, copper and silver.

7. A process according to claim 1, wherein the hydrodealkylation temperature is between 500° and 570° C. when hydrodealkylation is carried out catalytically.

8. A process according to claim 7, wherein the hydrodealkylation effluent is at least partially condensed and is then passed into a separation zone so as to obtain (a) a methane-rich gaseous phase from which are obtained a fraction containing hydrogen and a fraction containing ethane and methane, and (b) a liquid phase which is passed into a distillation zone to obtain at least a benzene cut constituting a usable product, and a toluene cut, at least a portion of the toluene cut being mixed with the fresh charge for passing into the first catalytic zone, and in which process at least a portion of said fraction containing hydrogen is passed together with a fresh charge, to the first catalytic bed.

9. A process according to claim 8, wherein at least a portion of said fraction containing hydrogen is also passed directly into the hydrodealkylation zone.

10. A process according to claim 5, wherein furthermore the heat released in said first catalytic zone is used to raise the temperature of the effluent from this first catalytic zone at least partway to the level required for carrying out the hydrodealkylation reaction.

* * * * *